United States Patent

Pourchez

[11] Patent Number: 6,001,079
[45] Date of Patent: Dec. 14, 1999

[54] MULTILUMEN CATHETER, PARTICULARLY FOR HEMODIALYSIS

[76] Inventor: Thierry Pourchez, 172 Boulevard Jean Moulin, 62400 Bethune, France

[21] Appl. No.: 09/029,251
[22] PCT Filed: Sep. 4, 1996
[86] PCT No.: PCT/FR96/01346
  § 371 Date: Mar. 9, 1998
  § 102(e) Date: Mar. 9, 1998
[87] PCT Pub. No.: WO97/09086
  PCT Pub. Date: Mar. 13, 1997

[30] Foreign Application Priority Data

Sep. 5, 1995 [FR] France .................................... 95 10573

[51] Int. Cl.$^6$ .............................. A61M 3/00; A61M 5/00
[52] U.S. Cl. .............................................. 604/43; 604/271
[58] Field of Search .................................. 604/27, 29, 28, 604/284, 19, 49, 54, 93, 258, 266, 264, 271, 239, 43; D24/108, 112; 600/581

[56] References Cited

U.S. PATENT DOCUMENTS

| | | | |
|---|---|---|---|
| 4,072,153 | 2/1978 | Swartz | 604/284 |
| 4,248,224 | 2/1981 | Jones . | |
| 4,309,994 | 1/1982 | Grunwald . | |
| 4,737,141 | 4/1988 | Spits | 604/28 |
| 4,925,452 | 5/1990 | Melinyshyn et al. | 604/284 |
| 5,041,101 | 8/1991 | Seder et al. | 604/264 |
| 5,100,395 | 3/1992 | Rosenberg | 604/284 |
| 5,120,304 | 6/1992 | Sasaki | 604/27 |
| 5,221,256 | 6/1993 | Mahurkar | 604/28 |
| 5,254,084 | 10/1993 | Geary | 604/29 |
| 5,378,230 | 1/1995 | Mahurkar | 604/43 |
| 5,458,582 | 10/1995 | Nakae | 604/27 |
| 5,569,182 | 10/1996 | Twardowski et al. | 604/43 |
| 5,599,304 | 2/1997 | Shaari | 604/284 |
| 5,776,111 | 7/1998 | Tesio | 604/29 |
| 5,797,869 | 8/1998 | Martin et al. | 604/177 |
| 5,807,311 | 9/1998 | Palestrant | 604/28 |

FOREIGN PATENT DOCUMENTS

| | | |
|---|---|---|
| 0453234 | 10/1991 | European Pat. Off. . |
| 9108132 | 9/1991 | Germany . |
| 9316741 | 2/1993 | WIPO . |
| 9316752 | 2/1993 | WIPO . |

OTHER PUBLICATIONS

American Cytoscope Makers, Inc., Catalogue of Catheters & Accessories, p. 64, 1960.

*Primary Examiner*—Wynn Wood Coggins
*Assistant Examiner*—Sharon Finkel
*Attorney, Agent, or Firm*—Kerkam, Stowell, Kondracki & Clarke, P.C.; John C. Kerins

[57] ABSTRACT

A multilumen catheter (1) of a type comprising two inner lumens (2, 3) defined by a wall (2A, 3A) for guiding a fluid (4), and two opposite ends (5, 6), namely a distal end (5) and a proximal end (6), characterized in that the distal end is formed of two elongated and discrete end portions (13, 14) located beyond a so-called dividing point (12) at a predetermined distance D1 from the proximal end (6), wherein said end portions, in a rest position of the catheter, extend parallel to the longitudinal axis thereof, each over a predetermined length (L1, L2) measurable between a free end (13A, 14A) and the dividing point (12), are each made of a flexible material, contain a segment of at least one lumen (2, 3) and have at least one channel (7, 8) for delivering and/or sampling the fluid.

3 Claims, 1 Drawing Sheet

MULTILUMEN CATHETER, PARTICULARLY FOR HEMODIALYSIS

BACKGROUND OF THE INVENTION

1. Field of the Invention

The invention relates to a device called a multilumen catheter, used for the circulation of a least one fluid between a cavity of a patient's body and a means for circulating this fluid such as a fluid perfusing and/or extracting means.

The invention relates more particularly, though not exclusively, to a catheter for hemodialysis.

2. Description of Related Art

The term multilumen catheter designates a catheter comprising at least two inner lumens defined by a wall, each of which is intended for guiding at least one fluid.

A catheter of this type also comprises two opposite ends, one of which is called a distal end since it is specifically intended to be placed in a cavity of a patient's body in order to deliver and/or sample the fluid to or from it through at least one channel, the other being called a proximal end, since it is specifically intended to be connected to a fluid circulating means such as a fluid perfusing and/or extracting means.

With the known catheters, the risk of clogging substances being deposited on the surfaces of the perfusing and/or extracting channels is substantial.

One object of the invention is to obtain a catheter having a risk of obstruction by clogging that is substantially reduced relative to the known catheters.

SUMMARY OF THE INVENTION

To this end, the subject of the invention is a catheter of the above-mentioned type, this catheter being characterized in that in order to constitute its distal end, it comprises, beyond a so-called dividing point located at a predetermined distance from its proximal end, at least two distinct elongated end portions which:

in at least one rest position of the catheter, extend substantially parallel to the longitudinal axis of this catheter, each over a predetermined length measurable between a free end and the dividing point, are each made of flexible material so as to be flexible at least under the effect of a lateral action due to the displacement of a fluid, contain at least one segment of at least one of the lumens and have at least one channel for delivering and/or sampling the fluid.

BRIEF DESCRIPTION OF THE DRAWING

The invention will be clearly understood by reading the following description given as a non-limiting example in reference to the appended drawing.

DETAILED DESCRIPTION OF THE PREFERRED EMBODIMENT

Figure 1:
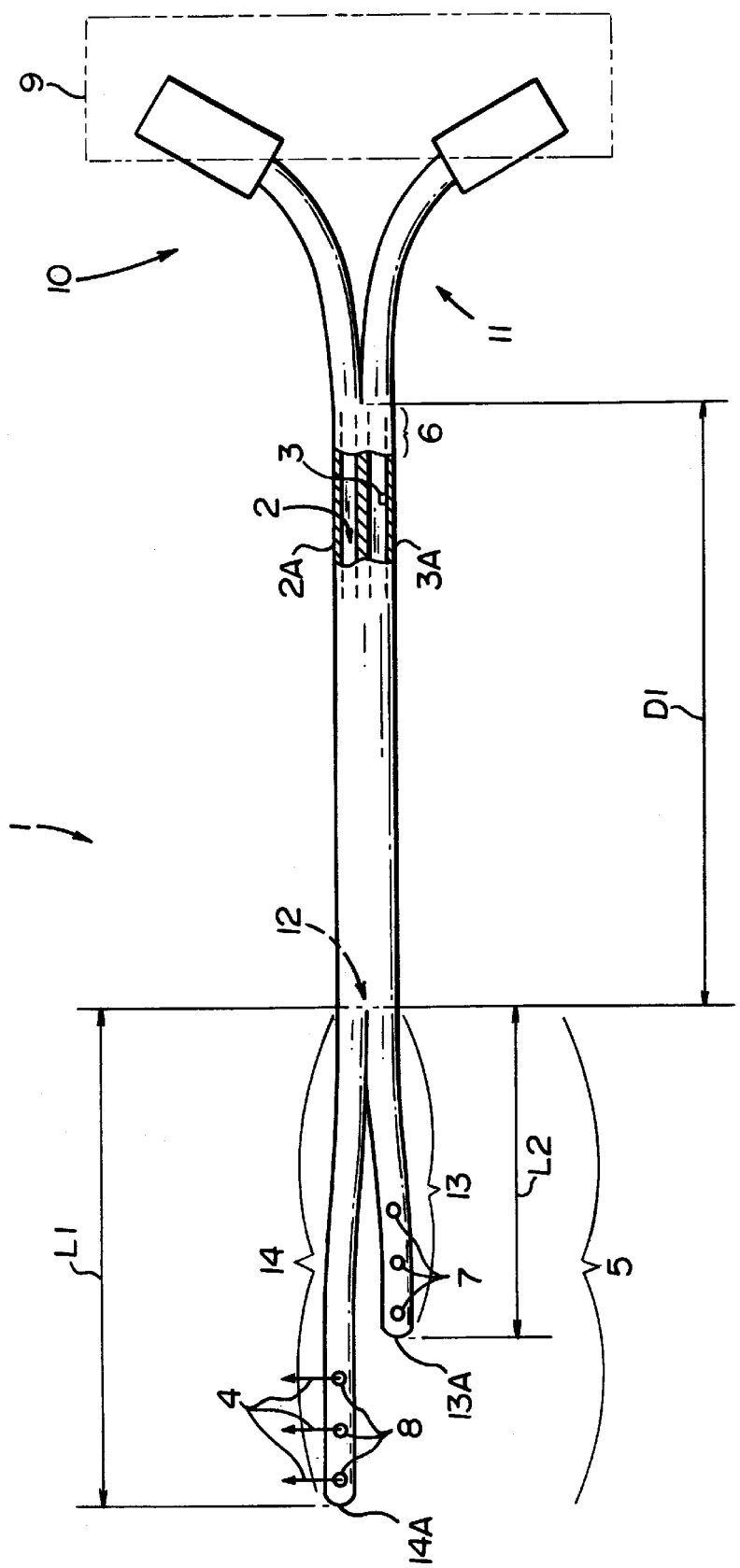
FIG. 1 is a side view of one embodiment of a catheter according to the invention.

The drawing shows an elongated device called a catheter 1 comprising:

at least two inner lumens 2, 3, defined by a wall 2A, 3A, each of which is intended for guiding at least one fluid 3, two opposite ends 5, 6, one of which 5 is called a distal end, since it is specifically intended to be placed inside a cavity of a patient's body (not represented) in order to deliver and/or sample the fluid 4 to or from it through at least one channel 7, 8, the other end 6 being called the proximal end, since it is specifically intended to be connected to a means 9 for circulating a fluid 4, such as a fluid perfusing and/or extracting means.

The fluid 4 is represented by arrows 4.

As shown, the channels 7, 8 are comprised of perforations disposed in the wall of the catheter that defines each of the lumens 2, 3.

These channels allow either the delivery into the area surrounding the catheter of a fluid contained in a lumen of this catheter, or the entry into a lumen of this catheter of a surrounding fluid.

For example, at least one of the lumens is intended for perfusing a fluid and at least one other lumen is intended for extracting fluid.

Also as shown, the lumens 2, 3 for circulating the fluid 4 are for example comprised of juxtaposed lumens, but this is not limiting for the invention.

The dimensions and proportions of the catheter represented are not limiting for the invention.

At its proximal end 6, the catheter has elements 10, 11 for connecting each of the lumens 2, 3 it comprises to the means 9 for circulating fluid 4.

As neither the circulating means 9 nor the elements 10, 11 for connecting to this means 9 are subjects of the invention, these elements 10, 11 and the means 9 are not represented in detail.

It is at the distal end 5 that the catheter of the invention is noteworthy.

In effect, in order to constitute its distal end, the catheter comprises, beyond a so-called dividing point 12 located at a predetermined distance D1 from its proximal end 6, at least two distinct elongated end portions 13, 14 which:

in at least one rest position of the catheter, extend substantially parallel to the longitudinal axis of this catheter, each over a predetermined length L1, L2 measurable between a free end 13A, 14A, and the dividing point 12, are each made of flexible material so as to be flexible at least under the effect of a lateral action due to the displacement of a fluid, contain at least one segment of at least one of the lumens 2, 3 and has at least one channel 7, 8 for delivering and/or sampling the fluid.

These technical characteristics, when the distal end of the catheter is placed on the axis of a fluid flow such as a bodily fluid flow, allow the end portions, due to their flexibility and independence, to act like a sail set parallel to the wind and thus are practically not subject to obstruction.

In effect, the agitation and flexion of these end portions considerably reduces the risk of clogging substances being deposited on the surfaces of the perfusing and/or extracting channels with which these end portions are equipped.

According to another noteworthy characteristic, the end portions have different lengths L1, L2, and the channels with which these end portions are equipped are disposed so that each of them emerges at a different level of the catheter.

According to another characteristic of the invention, the channels with which the end portions are equipped are disposed in a group on each end portion, and these groups are disposed at different levels of the catheter.

I claim:

1. A multilumen catheter (1) comprising:

at least two inner lumens (2, 3), defined by a wall (2A, 3A), each of said inner lumens being adapted to guide at least one fluid (4), said wall isolating said at least two inner lumens from one another along an entire length of said catheter, to define at least two separate fluid flow passages, two opposite ends (5, 6), a first one of which (5) is a distal end, said distal end specifically intended to be placed in a cavity of a patient's body and adapted to deliver and/or sample the fluid (4) to or from said distal end through at least one channel (7,8), a second end (6) being a proximal end, said proximal end adapted to be connected to a means (9) for circulating fluid (4), said distal end of said catheter having a dividing point (12) located at a fixed predetermined distance D1 from said proximal end (6), and having at least two distinct elongated end portions (13, 14) extending from said dividing point, said dividing point being nearer to said distal end than to said proximal end, wherein said at least two end portions, in at least one rest position of the catheter, extend substantially parallel to a longitudinal axis of said catheter, each over a predetermined length (L1, L2) measurable between a free end of said distal end (13A, 14A) and the dividing point (12), wherein said at least two end portions are each made of flexible material so as to be flexible at least under the effect of a lateral action due to the displacement of a fluid, and wherein each of said at least two end portions contains at least one segment of at least one of the lumens (2, 3) and has at least one channel (7, 8) for delivering and/or sampling the fluid.

2. The multilumen catheter according to claim 1, wherein:

each of said at least two end portions has a different length (L1, L2), and the channels with which each of said at least two end portions are equipped are so constructed and arranged such that each emerges at a different position along the catheter.

3. The multilumen chatheter according to claim 2, wherein the channels with which the at least two end portions are equipped are disposed in a group on each end portion, and wherein said groups are disposed at different positions along the catheter.

\* \* \* \* \*

UNITED STATES PATENT AND TRADEMARK OFFICE
CERTIFICATE OF CORRECTION

PATENT NO.    : 6,001,079
DATED         : December 14, 1999
INVENTOR(S)   : Thierry Pourchez It is certified that error appears in the above-identified patent and that said Letters Patent is hereby corrected as shown below:

Title page,
Item [87], "§371 Date: Mar. 9, 1998" should be -- §371 Date: Mar. 5, 1998 --.
Item [87], "§102 (e) Date: Mar. 9, 1998" should be -- §102(e) Date: Mar. 5, 1998 --.

Column 4,
Line 17, "chatheter" should be -- catheter --.

Signed and Sealed this

Fourth Day of June, 2002

Attest:

JAMES E. ROGAN
Attesting Officer                Director of the United States Patent and Trademark Office

(12) EX PARTE REEXAMINATION CERTIFICATE (5846th)
United States Patent
Pourchez

(10) Number: US 6,001,079 C1
(45) Certificate Issued: Aug. 7, 2007

(54) MULTILUMEN CATHETER, PARTICULARLY FOR HEMODIALYSIS

(76) Inventor: Thierry Pourchez, 172 Boulevard Jean Moulin, 62400 Bethune (FR)

Reexamination Request:
No. 90/006,737, Aug. 8, 2003
No. 90/006,798, Oct. 3, 2003

Reexamination Certificate for:
Patent No.: 6,001,079
Issued: Dec. 14, 1999
Appl. No.: 09/029,251
Filed: Mar. 5, 1998

Certificate of Correction issued Jun. 4, 2002.

(22) PCT Filed: Sep. 4, 1996
(86) PCT No.: PCT/FR96/01346
§ 371 (c)(1),
(2), (4) Date: Mar. 5, 1998
(87) PCT Pub. No.: WO97/09086
PCT Pub. Date: Mar. 13, 1997

(30) Foreign Application Priority Data

Sep. 5, 1995 (FR) .............................. 95 10573

(51) Int. Cl.
*A61M 3/00* (2006.01)
*A61M 5/00* (2006.01)

(52) U.S. Cl. ......................................... 604/43; 604/271
(58) Field of Classification Search ................... 604/27, 604/29, 28, 284, 19, 49, 54, 93, 258, 266, 604/264, 271, 239, 43; D24/108, 112; 600/581
See application file for complete search history.

(56) References Cited

U.S. PATENT DOCUMENTS

| | | | |
|---|---|---|---|
| 1,856,811 | A | 5/1932 | Inaki |
| 2,286,462 | A | 6/1942 | Chaffin |
| 2,910,981 | A | 11/1959 | Wilson et al. |
| 3,144,868 | A | 8/1964 | Jascalevich |
| 3,256,885 | A | 6/1966 | Higgins et al. |
| 4,134,402 | A | 1/1979 | Mahurkar |
| 4,385,631 | A | 5/1983 | Uthmann |
| 4,405,313 | A | 9/1983 | Sisley et al. |
| 4,451,252 | A | 5/1984 | Martin |
| 4,493,696 | A | 1/1985 | Uldall |
| RE31,873 | E | 4/1985 | Howes |
| 4,543,087 | A | 9/1985 | Sommercorn et al. |

(Continued)

FOREIGN PATENT DOCUMENTS

| | | |
|---|---|---|
| DE | 88 15 869 U1 | 2/1989 |
| EP | 0 132 344 A2 | 1/1985 |
| EP | 0 33 2 366 A2 | 9/1989 |
| EP | 0 386 408 A1 | 9/1990 |
| EP | 0 453 234 B1 | 10/1991 |
| EP | 0 711 574 A1 | 5/1996 |
| SU | 459237 A | 2/1975 |

OTHER PUBLICATIONS

Transcript of Videotaped Deposition of John Zawacki, Sep. 16–17, 2003, *Thierry Pourchez and Bard Access Systems, Inc. v. Diatek, Inc. and Arrow International, Inc.*, Civil Action No. 03–CV–0972 (S.D.N.Y.).

(Continued)

*Primary Examiner*—Cris Rodriguez

(57) ABSTRACT

A multilumen catheter (1) of a type comprising two inner lumens (2, 3) defined by a wall (2A, 3A) for guiding a fluid (4), and two opposite ends (5, 6), namely a distal end (5) and a proximal end (6), characterized in that the distal end is formed of two elongated and discrete end portions (13, 14) located beyond a so-called dividing point (12) at a predetermined distance D1 from the proximal end (6), wherein said end portions, in a rest position of the catheter, extend parallel to the longitudinal axis thereof, each over a predetermined length (L1, L2) measurable between a free end (13A, 14A) and the dividing point (12), are each made of a flexible material, contain a segment of at least one lumen (2, 3) and have at least one channel (7, 8) for delivering and/or sampling the fluid.

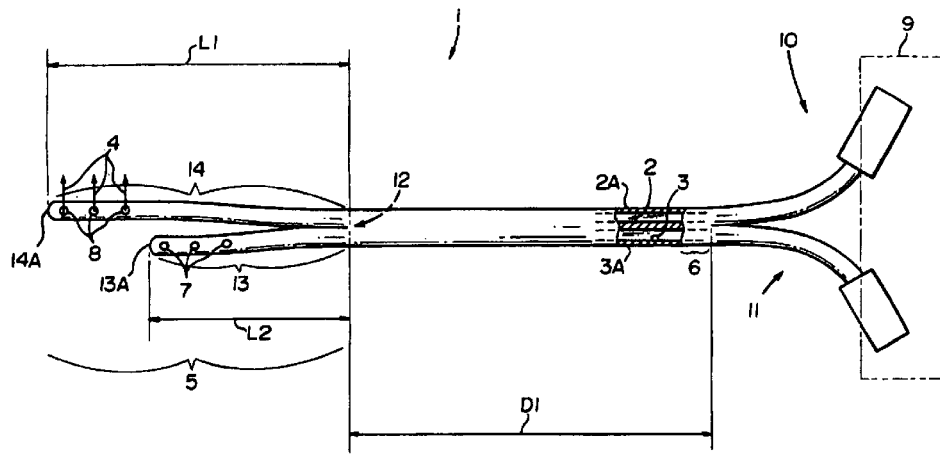

U.S. PATENT DOCUMENTS

| Patent No. | Date | Inventor |
|---|---|---|
| 4,568,329 A | 2/1986 | Mahurkar |
| 4,583,968 A | 4/1986 | Mahurkar |
| 4,623,327 A | 11/1986 | Mahurkar |
| 4,626,240 A | 12/1986 | Edelman et al. |
| 4,643,711 A | 2/1987 | Bates |
| 4,675,004 A | 6/1987 | Hadford et al. |
| 4,681,564 A | 7/1987 | Landreneau |
| 4,681,570 A | 7/1987 | Dalton |
| 4,682,978 A | 7/1987 | Martin |
| 4,687,471 A | 8/1987 | Twardowski et al. |
| 4,692,141 A | 9/1987 | Mahurkar |
| 4,770,652 A | 9/1988 | Mahurkar |
| 4,772,268 A | 9/1988 | Bates |
| 4,804,359 A * | 2/1989 | Grunwald et al. ......... 604/6.16 |
| 4,808,155 A | 2/1989 | Mahurkar |
| 4,820,265 A | 4/1989 | DeSatnick et al. |
| 4,867,742 A | 9/1989 | Calderon |
| 4,895,561 A | 1/1990 | Mahurkar |
| 5,053,003 A | 10/1991 | Dadson et al. |
| 5,053,004 A | 10/1991 | Markel et al. |
| 5,053,023 A | 10/1991 | Martin |
| 5,084,013 A | 1/1992 | Takase |
| 5,098,412 A | 3/1992 | Shiu |
| 5,106,368 A * | 4/1992 | Uldall et al. ................... 604/43 |
| 5,156,592 A | 10/1992 | Martin et al. |
| 5,171,216 A | 12/1992 | Dasse et al. |
| 5,190,520 A | 3/1993 | Fenton, Jr. et al. |
| 5,197,951 A | 3/1993 | Mahurkar |
| 5,209,723 A | 5/1993 | Twardowski et al. |
| 5,221,255 A | 6/1993 | Mahurkar et al. |
| 5,273,534 A | 12/1993 | Knoepfler |
| 5,279,599 A | 1/1994 | Wilk |
| 5,318,517 A | 6/1994 | Reiman |
| 5,322,519 A | 6/1994 | Ash |
| 5,360,397 A | 11/1994 | Pinchuk |
| 5,374,245 A | 12/1994 | Mahurkar |
| 5,405,320 A | 4/1995 | Twardowski et al. |
| 5,405,341 A | 4/1995 | Martin |
| 5,451,206 A | 9/1995 | Young |
| 5,472,432 A | 12/1995 | Martin |
| 5,476,453 A | 12/1995 | Mehta |
| 5,486,159 A | 1/1996 | Mahurkar |
| 5,509,897 A | 4/1996 | Twardowski et al. |
| 5,509,902 A | 4/1996 | Raulerson |
| 5,556,390 A | 9/1996 | Hicks |
| 5,584,803 A | 12/1996 | Stevens et al. |
| 5,685,867 A | 11/1997 | Twardowski et al. |
| 5,695,457 A | 12/1997 | St. Goar et al. |
| 5,704,915 A | 1/1998 | Melsky et al. |
| 5,713,853 A | 2/1998 | Clark et al. |
| 5,718,692 A | 2/1998 | Schon et al. |
| 5,807,318 A | 9/1998 | St. Goar et al. |

OTHER PUBLICATIONS

Nonconfidential exhibits (D–10, D–14, D–15, D–16, D–20, D–32, D–41) in Deposition of John Zawacki, Sep. 16–17, 2003, *Thierry Pourchez and Bard Access Systems, Inc. v. Diatek, Inc. and Arrow International, Inc.*, Civil Action No. 03–CV–0972 (S.D.N.Y.).

Bander, et al., *Central Venous Angioaccess for Hemodialysis and Its Complications*, Seminars in Dialysis, 1992, vol. 5, No. 2, pp. 121–128.

Baranowski, L., *Central Venous Access Devices*, Journal of Intravenous Nursing, 1993, vol. 16, No. 3, pp. 167–194.

Berkoben, et al., *Maintenance of Permanent Hemodialysis Vascular Access Patency*, ANNA Journal, 1995, vol. 22, No. 1, pp. 17–24.

Bolz, et al., *Catheter Malfunction and Thrombus Formation on Double–Lumen Hemodialysis Catheters: An Intravascular Ultrasonographic Study*, American Journal of Kidney Diseases, 1995, vol. 25, No. 4, pp. 597–602.

Bour, et al., *Experience With The Double Lumen Silastic® Catheter For Hemoaccess*, Surgery, Gynecology & Obstetrics, 1990, vol. 171, pp. 33–39.

Campbell, et al., *Radiological Insertion of Long–term Venous Access Devices*, Seminars in Interventional Radiology, 1994, vol. II, No. 4, pp. 366–375.

Donaldson, et al., *Peripherally Inserted Central Venous Catheters: US–guided Vascular Access in Pediatric Patients*[1], Radiology, 1995, vol. 197, pp. 542–544.

Dunea, et al., *A Survey of Permanent Double Lumen Catheters in Hemodialysis Patients*, ASAIO Transac. 1991:37:M276–7.

Dupont et al, "Long–Term Development of Permcath Quinton Catheter" [French] Néphrologie 15: 105–10 (1994) (with English summary).

Gallichio, et al., *Placement of a Double Lumen Silastic Catheter for Hemodialysis Access Through The Cephalic Vein*, Journal of the American College of Surgeons, 1994, vol. 179, pp. 171–172.

Gravenstein, et al., *In Vitro Evaluation of Relative Perforating Potential of Central Venous Catheters: Comparison of Materials, Selected Models, Number of Lumens, and Angles of Incidence to Simulated Membrane*, Journal of Clinical Monitoring, 1991, vol. 7, pp. 1–6.

Haindl, H., *Technical complications of port–catheter systems*, Reg. Cancer Treat, 1989, 2:238–242.

Haire, et al., *Thrombotic Complications of Subclavian Apheresis catheters in Cancer Patients: Prevention With Heparin Infusion*, Journal of Clinical Apheresis, 1990, vol. 5, pp. 188–191.

Hull, et al., *The Groshong Catheter: Initial Experience and Early Results of Imaging–guided Placement*[1], Radiology, 1992, vol. 185, pp. 803–807.

Ignotus, et al., *Review of Radiological Insertion of Indwelling Central Venous Catheters*, Minimally Invasive Therapy, 1992, 1:373–388.

Jones, et al., *Efficacy of the Supraclavicular Route for Temporary Hemodialysis Access*, Southern Medical Journal, 1992, vol. 85, No. 7, pp. 725–726.

Kaupke, et al., *Perforation of the Superior Vena Cava By a Subclavin Hemodialysis Catheter: early detection by angiography*, The International Journal of Artificial Organs, 1992, vol. 15, No. 11, pp. 666–668.

Kelber, et al., *Factors Affecting Delivery of High–Efficiency Dialysis Using Temporary Vascular Access*, American Journal of Kidney Diseases, 1993, vol. 22, No. 1, pp. 24–29.

Lumsden, et al., *Hemodialysis Access in the Pediatric Patient Population*, The American Journal of Surgery, 1994, vol. 168, pp. 197–201.

Lund, et al., *Percutaneous Translumber Inferior Vena Cava Cannulation for Hemodialysis*, American Journal of Kidney Diseases, 1995, vol. 25, No. 5, pp. 732–737.

Lund, "Percutaneous Translumber Inferior Vena Cava Cannulation and other Alternative Vascular Access Techniques" in Venous Interventional Radiology with Clinical Perspectives, Savader et al, eds, pp. 251–61 (date unknown).

Maki, D., *Pathogenesis, Prevention, and Management of Infections Due to Intravascular Devices Used for Infusion Therapy*, in Infections Associated with Indwelling Medical Devices, Bisno et al, eds, American Society for Microbiology, 1989, pp. 161–177.

Mauro, et al., *Radiologic Placement of Long–term Central Venous Catheters: A Review*, JVIR, 1993, vol. 4, No. 1, pp. 127–137.

McGee, et al., *Accurate placement of central venous catheters: A prospective, randomized, multicenter trial*, Critical Care Medicine, 1993, vol. 21, No. 8, pp. 1118–1123.

Moss, et al., *Use of a Silicone Catheter With a Dacron Cuff for Dialysis Short–Term Vascular Access*, American Journal of Kidney Diseases, 1988, vol. XII, No. 6, pp. 492–498.

Northsea, C., *Using Urokinase to Restore Patency in Double Lumen Catheters*, ANNA Journal 1994, vol. 21, No. 5, pp. 261–273.

Parsa, et al., *Establishment of Intravenous Lines for Long–term Intravenous Therapy and Monitoring*, Surgical Clinics of N. Am. 1985, vol. 65, No. 4, pp. 835–865.

Parsa, et al., *Vascular Access Techniques*, Monitoring, pp. 122–145 (date unknown).

Pasquale, et al., *Groshong® Versus Hickman® Catheters*, Surgery, Gynecology & Obstetrics, 1992, vol. 174, pp. 408–410.

Passaro, et al., *Long–term Silastic Catheters and Chest Pain*, Journal of Parenteral and Enteral Nutrition, 1994, vol. 18, No. 3, pp. 240–242.

Paulsen, et al., *Use of Tissue Plasminogen Activator for Reopening of Clotted Dialysis Catheters*, Nephron, 1993, vol. 64, pp. 468–470.

QUINTON® Catheter Products (1993).

Raaf, et al., *Open Insertion of Right Atrial Catheters Through the Jugular Veins*, Surgery, Gynecology & Obstetrics, 1993, vol. 177, pp. 295–298.

Schwab, et al., *Prospective Evaluation of a Dacron Cuffed Hemodialysis Catheter for Prolonged Use*, American Journal of Kidney Diseases, 1998, vol. XI, No. 2, pp. 166–169.

Shaffer, D., *Catheter–Related Sepsis Complicating Long–Term Tunnelled Central Venous Dialysis Catheters: Management by Guidewire Exchange*, American Journal of Kidney Diseases, 1995, vol. 25, No. 4, pp. 593–596.

Shaffer, D., *Lessons From Vascular Access Procedures for Hemodialysis*, Surgical Oncology Clinics of North America, 1995, vol. 4, No. 3, pp. 537–549.

Sioshansi, P., *New Processes for Surface Treatment of Catheters*, Artificial Organs, 1994, 18(4):266–271.

Schwab, et al., *Vascular Access: Case Oriented Discussions of Selected Critical Issues: Hemodialysis Catheters for Permanent Use* (date unknown).

Swartz, et al., *Successful Use of Cuffed Centrol Venous Hemodialysis Catheters Inserted Percutaneously*, J. Am. Soc. Nephrol., 1994, 4:1719–1725.

Tesio, et al., *Double Catheterization of the Internal Jugular Vein for Hemodialysis: Indications, Techniques, and Clinical Results*, Articial Organs, 1994, vol. 18, No. 4, pp. 301–304.

Treiman, et al., *Chronic Venous Access in Patients with Cancer*, Cancer, 1993, vol. 72, No. 3, pp. 760–765.

Twadorski et al., "Blood Recirculation in Intravenous Catheters for Hemodialysis" J. Am. Soc. Nephrol. 3:1978–81 (1993).

Uldall, P., *Subclavian Cannulation Is No Longer Necessary or Justified in Patients with End–Stage Renal Failure*, Seminars in Dialysis, 1994, vol. 7, No. 3, pp. 161–164.

Wechsler, et al., *Thrombosis and Infection Caused by Thoracic Venous Catheters: Pathogenesis and Imagings Findings*, AJR, 1993; 160:467–471.

Weitzel, et al., *Successful Use of Indwelling Cuffed Femoral Vein Catheters in Ambulatory Hemodialysis Patients*, American Journal of Kidney Diseases, 1993, vol. 22, No. 3, pp. 426–429.

Transcript of Videotaped Deposition of Thierry Pourchez, vol. 1, Oct. 16, 2003, *Thierry Pourchez and Bard Access Systems, Inc. v. Diatek, Inc. and Arrow International, Inc.*, Civil Action No. 03–CV–0972 (S.D.N.Y.).

Transcript of Videotaped Deposition of Thierry Pourchez, vol. 2, Oct. 17, 2003, *Thierry Pourchez and Bard Access Systems, Inc. v. Diatek, Inc. and Arrow International, Inc.*, Civil Action No. 03–CV–0972 (S.D.N.Y.).

Defendant's Exhibit DX78–DX114, *Thierry Pourchez and Bard Access Systems, Inc. v. Diatek, Inc. and Arrow International, Inc.*, Civil Action No. 03–CV–0972 (S.D.N.Y.).

Defendants' Responses and Objections to Plaintiffs' Second Set of Interrogatories (Excerpt), *Thierry Pourchez and Bard Access Systems, Inc. v. Diatek, Inc. and Arrow International, Inc.*, Civil Action No. 03–CV–0972 (S.D.N.Y.).

Transcript of Videotaped Deposition of Gregory Haas (Excerpt), Sep. 23, 2003, *Thierry Pourchez and Bard Access Systems, Inc. v. Diatek, Inc. and Arrow International, Inc.*, Civil Action No. 03–CV–0972 (S.D.N.Y.).

Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow Internations, Inc.*, Civil Action No. 03–CV–0972 (S.D.N.Y.).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3 is confirmed.

New claims 4–15 are added and determined to be patentable.

*4. The multilumen catheter of claim 1, wherein at least one of the lumens has a plurality of channels for delivering and/or sampling the fluid.*

*5. The multilumen catheter of claim 4, wherein the plurality of channels in the at least one lumen is arranged in a straight line along the respective lumen.*

*6. The multilumen catheter of claim 4, wherein the plurality of channels pass through a side wall of the at least one of the lumens.*

*7. The multilumen catheter of claim 4, wherein each lumen has a plurality of channels for delivering and/or sampling the fluid.*

*8. The multilumen catheter of claim 7, wherein each plurality of channels pass through a side wall of the respective lumen.*

*9. The multilumen catheter of claim 7, wherein the plurality of channels in each lumen is arranged in a straight line along the respective lumen.*

*10. The multilumen catheter of claim 1, wherein the at least one channel of at least one end portion passes through a side wall of that end portion.*

*11. The multilumen catheter of claim 10, wherein the at least one channel of each end portion passes through a side wall of the respective end portion.*

*12. The multilumen catheter of claim 1, wherein said at least two end portions are each made of flexible material so as to be flexible at least under the effect of a lateral action due to the displacement of blood.*

*13. The multilumen catheter of claim 1, wherein the proximal end comprises connector elements adapted to be connected to the means for circulating fluid.*

*14. The multilumen catheter of claim 13, wherein the connector elements are spaced apart.*

*15. The multilumen catheter of any one of claims 1 and 3–14, wherein each of the at least two end portions has a different length (L1, L2).*

\* \* \* \* \*